United States Patent
Flucke (10) Patent No.: US 11,591,560 B2
(45) Date of Patent: Feb. 28, 2023

(54) MANUAL INJECTOR FOR CELL MANIPULATION

(71) Applicant: Eppendorf AG, Hamburg (DE)

(72) Inventor: Christian Flucke, Hamburg (DE)

(73) Assignee: Eppendorf AG, Hamburg (DE)

( * ) Notice: Subject to any disclaimer, the term of this patent is extended or adjusted under 35 U.S.C. 154(b) by 776 days.

(21) Appl. No.: 16/069,605

(22) PCT Filed: Dec. 22, 2017

(86) PCT No.: PCT/EP2017/084420
§ 371 (c)(1),
(2) Date: Jul. 12, 2018

(87) PCT Pub. No.: WO2018/115457
PCT Pub. Date: Jun. 28, 2018

(65) Prior Publication Data
US 2019/0309252 A1 Oct. 10, 2019

(30) Foreign Application Priority Data
Dec. 23, 2016 (EP) ..................................... 16206714

(51) Int. Cl.
*C12M 1/26* (2006.01)
*C12M 1/42* (2006.01)
(Continued)

(52) U.S. Cl.
CPC ............ *C12M 35/00* (2013.01); *G02B 21/32* (2013.01); *C12M 23/50* (2013.01); *C12M 33/04* (2013.01)

(58) Field of Classification Search
CPC ..... C12M 33/04; B01L 3/02; A61M 5/31576; A61M 5/31586
See application file for complete search history.

(56) References Cited

U.S. PATENT DOCUMENTS 5,456,388 A * 10/1995 Honstein ........... A61M 5/31525
604/227
7,193,521 B2 * 3/2007 Moberg ................ A61M 39/12
340/679
(Continued)

FOREIGN PATENT DOCUMENTS

EP 1544286 A1 6/2005

OTHER PUBLICATIONS

Research Instruments: "SAS-SE Air Syringe", Apr. 27, 2010, OP002771875, Gefunden im Internet: URL:http://steptoemd.com/injector2.pdf [gefunden am Jul. 10, 2017] das ganze Dokument.
(Continued)

*Primary Examiner* — Jonathan M Hurst
(74) *Attorney, Agent, or Firm* — Edwin E. Voigt, II; Richard A. Arrett (57) ABSTRACT

A manual injector for cell manipulation comprising a displacement device for displacing a fluid, an injection tube connected to the displacement device, and a capillary holder connected to the injection tube for holding a microcapillary tube or a microcapillary tube connected to the injection tube, wherein the displacement device has the following: a disk-shaped main body that, on a first end face, has an hollow cylinder space which is concentric with its middle axis, a disk-shaped adjusting wheel, a helical gear, a hollow cylindrical plunger, a rotational decoupling that connects the adjusting wheel to the plunger, and a connection connected to the cylinder space to which the injection tube is connected.

17 Claims, 4 Drawing Sheets

(51) Int. Cl.
  *G02B 21/32* (2006.01)
  *C12M 1/00* (2006.01)

(56) References Cited

U.S. PATENT DOCUMENTS 9,366,241 B2 * 6/2016 Tschanz .................. H02K 7/06
2003/0160072 A1 * 8/2003 Geiser ............... A61M 5/31586
  222/327

OTHER PUBLICATIONS

Eppendorf: "CellTram Air CellTram Oil Cell tram Vario Operating manual", Jan. 31, 2009, XP002771876, Gefunden im Internet: URL:http://www.pocdscientific.com.au/files/POCDS_pdfs/CellTram_AirOilVario_operatingmanual.pdf [gefunden am Jul. 10, 2017] Seite 5-Seite 18.
Narishige: "IM-11-2 Pneumatic Microinjector", Jan. 31, 1999, XP002771877, Gefunden im Internet: URL:http://products.narishige-group.com/group1/IM-11-2/injection/english.html [gefunden am Jul. 10, 2017] das ganze Dokument.

\* cited by examiner

MANUAL INJECTOR FOR CELL MANIPULATION

The invention relates to a manual injector for cell manipulation, as well as a method for cell manipulation and the use of the manual injector.

Typical tasks in cell manipulation are holding cells, injecting solutions, cells and cell components into cells or tissue, and removing or taking up cells, cell components or solutions. Injectors (microinjectors) are used for this. These comprise a displacement device for a fluid that is connected via a tube to a capillary holder to hold an exchangeable microcapillary tube. A manual injector has a manually driven displacement device. A microcapillary tube is a hollow needle with a tip that has an inner diameter within the range of 1 to 200 µm, preferably 4 to 100 µm. Preferably, the microcapillary tube consists of glass.

By means of the displacement device, underpressures or overpressures are generated in the microcapillary tube in order to hold, remove or inject cells, cell components or solutions by means of the microcapillary tube. For injection, a microcapillary tube can be inserted into a cell. In so doing, the cell that floats in the cell medium can be held by means of another microcapillary tube. One example of use is in-vitro fertilization in which a sperm cell is injected by means of a microcapillary tube into an egg cell held by means of another microcapillary tube.

Known workplaces for cell manipulation comprise an inverse microscope for visualizing the cells and a movable microscope table mounted thereupon for placing the cells in the field of vision. One to two manipulators are fastened to the microscope and transfer the hand movements of the user with a high reduction ratio to microcapillary tubes as a tool for manipulating the cells. In the known workplaces, all of the components are arranged very closely next to each other on a vibration-dampened work table. Manual injectors are, however, relatively large. Due to the sizes and the design and arrangement of the control elements, known manual injectors are comparatively user-unfriendly.

With pneumatic microinjectors, the fluid is air or another gas. The pneumatic microinjector CellTram® Air by Eppendorf AG and the pneumatic microinjector IM11-2 by the Narishige Group have, sequentially in an axial direction, a setting wheel, a threaded spindle which can be adjusted in a spindle nut, and a plunger in a cylinder. The setting wheel is located at one end of a cylindrical housing that contains the threaded spindle, spindle nut, plunger and cylinder. The housing is oriented substantially horizontally, wherein it is mounted slightly pivotable about a horizontal axis on a device foot. By adjusting the setting wheel, the plunger is displaced within the cylinder, and an air column is shifted within the microcapillary tube. It is disadvantageous that, to adjust the setting wheel, the user must assume an ergonomically unfavorable posture in which the shoulders are raised, the lower arm is lifted off the table, and the wrist is angled. If he works with two injectors, he must assume the posture with both shoulders and arms.

Furthermore, the performance of pneumatic injectors is limited by the compressibility of air, and by leakages from poor designs or deficient devices. Due to compression or leakages, the air pressure can gradually change within the system (drift), and the holding of cells and removal and injection of material can be impaired.

Moreover, most pneumatic injectors have an unfavorable ratio of the working volume of the plunger/cylinder unit to the dead volume in the system, which further restricts performance. Users frequently feel that conventional pneumatic injectors are sluggish and not optimal for dynamic manipulation tasks, i.e., to be performed with a minimum delay, such as capturing and immobilizing sperm or injecting into cells. In particular, they are felt to be sluggish for changes to be performed in rapid sequence between different pressures, in particular when changing between overpressures and/or underpressures.

If the threaded spindle has a steep thread, precise volume settings are difficult. If it has a fine thread, numerous rotations of the setting wheel are needed for cell manipulation.

The pneumatic microinjector IM11-2 by the Narishige Group has two coaxial threaded spindles, one of which has a steep thread and the other of which has a fine thread that optionally enable both a rapid dosing of large volumes as well as a fine dosing of small volumes. However, the highly complex design is disadvantageous, especially since an additional friction element made of plastic that acts as a brake on the steep threaded spindle prevents the compressed air in the cylinder space from moving the plunger since the self-locking of the threaded spindle/spindle nut pair is insufficient.

The pneumatic microinjectors SAS and SAS-SE by Research Instruments Ltd. have a columnar adjusting wheel that is connected via a threaded spindle that can be rotated in a spindle nut to a plunger arranged therebelow in a cylinder. The adjusting wheel is adjusted with the thumb and forefinger. Below the columnar adjusting wheel, the microinjector has a disk-shaped base. Due to the high transmission ratio, a quick adjustment of larger volumes is in fact possible. However, a precise adjustment of small volumes is difficult.

With hydraulic microinjectors, the fluid is a liquid. The manual microinjector CellTram® Oil by Eppendorf AG and other hydraulic injectors work with a liquid as the displacement fluid. A small air cushion in the microcapillary tube prevents direct contact between the liquid and the material to be handled. In contrast to pneumatic injectors, the avoidance of drift from compression effects and the nearly delay-free shifting of the liquid is advantageous. A disadvantage is, however, that the hydraulic injector must be filled with liquid free of bubbles, and filling must be repeated after a certain number of manipulations. In addition, there is the danger of contaminations and incompatibilities from the contact between liquid and cells.

With pneumatic and hydraulic microinjectors, play between the threaded spindle and spindle nut can cause a hysteresis.

Against this backdrop, the object of the invention is to provide a manual injector for displacing a fluid for cell manipulation that is more user-friendly, has low drift without using a hydraulic medium, enables dynamic, i.e., low-delay working, and enables a displacement of large volumes with minor adjustment effort and a precise adjustment of small volumes.

The object is achieved by a manual injector with the features of the invention disclosed herein.

The manual injector according to the invention for cell manipulation comprises a displacement device for displacing a fluid, an injection tube connected to the displacement device, and a capillary holder connected to the injection tube for holding a microcapillary tube, or a microcapillary tube connected to the injection tube, wherein the displacement device has the following features:
 a disk-shaped main body that, on a first end face, has an annular cylinder space which is concentric with its middle axis, a disk-shaped adjusting wheel which is concentric with the main body and is arranged on the first end face, a helical gear comprising a spindle nut and a threaded spindle engaging therein and arranged on the middle axis of the main body, wherein the spindle nut is securely connected to the adjusting wheel, and the threaded spindle is securely connected to the main body or vice versa, a hollow cylindrical plunger arranged in the cylinder space, and sealingly adjacent to the inner perimeter of the inner wall of the cylinder space and the outer perimeter of the outer wall of the cylinder space, a rotational decoupling that connects the adjusting wheel to the plunger and is designed such that the plunger and adjusting wheel are not displaceable relative to each other in the direction of the middle axis of the main body, and are rotatable relative to each other about the middle axis, and a connection connected to the cylinder space to which the injection tube is connected.

The displacement device of the injector according to the invention can be placed on a worktable or another base so that the main body is arranged below and the adjusting wheel above. The displacement device is driven manually by rotating the adjusting wheel relative to the main body. The rotation of the adjusting wheel is translated into a linear movement by the spindle nut and the threaded spindle such that the adjusting wheel is displaced in the direction of the middle axis of the main body closer thereto or away therefrom. By means of the rotational decoupling, the adjusting wheel thereby entrains the plunger, which ejects a fluid out of the cylinder space or draws it thereinto. The rotational decoupling thereby causes the adjusting wheel to displace the plunger in the direction of the middle axis of the main body and not to rotate about the middle axis. Preferably, the injector is a pneumatic injector, and the fluid is air or another gas. The injector can, however, also be a hydraulic injector, and the fluid can be a liquid. By displacing the fluid, medium can be drawn by a microcapillary tube or discharged therefrom via an injection tube connected to the connection.

The displacement device has a flat design since the helical gear, the main body with the cylinder space and the adjusting wheel with the plunger are arranged nested coaxially in each other. During operation, the arm of the user can lie in an ergonomic position on the table next to the displacement device. At the same time, the back of the hand can be supported by the table. The displacement device can be operated by tilting the hand and rotating the adjusting wheel with the fingers. Relative to the dimensions of the displacement device, the working volume that can be displaced by displacing the plunger in the cylinder space is comparatively large. This property results from the particularly large diameters of the surface area of the cylinder space and the plunger. Furthermore, only a small stroke of the plunger is required to achieve a large volume displacement. A comparatively large volume can be displaced relative to a rotation of the adjusting wheel. On the other hand, the displaced volume per arc element on the perimeter of the adjusting wheel is comparatively small so that very sensitive operation is also possible. In comparison to the working volume (such as 20 mL), the injector has a very small dead volume (e.g. 0.5 mL including 1.3 m of the tube and capillary holder) such that high pressures can be achieved and held quickly despite pneumatic operation. The working volume is the amount of space that can be displaced by the plunger in the cylinder from a maximum stroke. The dead volume consists of ancillary spaces such as the inner volume of the capillary holder, the injection tube, or connections, and cannot be displaced. The working and dead volumes are, however, not in a causal relationship, i.e., they do not scale to each other. However, in the present invention, the dead volume is comparatively smaller than the working volume. In particular, the dead volume in the device according to the invention is less than or equal to 1 mL.

Due to the simple design, the production costs can be kept down. The displacement device is scalable such that, for example, small embodiments are possible that only serve to hold cells and can be accommodated in a space-saving manner at a workplace for cell manipulation (for example by being attached, in particular adhered to a microscope or a control panel of a manipulator). Furthermore, large embodiments can be realized that in particular can be used to inject materials into cells.

The displacement device can be designed to be particularly space saving, for example with a maximum height of 5 cm, preferably within the range of 3 to 4 cm, and with a diameter of 30 to 130 mm, preferably from 80 to 100 mm for injectors for dynamic uses, and preferably 40 to 60 mm for injectors for holding cells.

According to a preferred embodiment of the invention, a combined linear and pivot bearing is present between the main body and adjusting wheel that is designed to guide the adjusting wheel in the direction of the middle axis of the main body when displaced relative to the main body, and to radially bear the adjusting wheel about the middle axis of the main body. A particularly precise displacement of the plunger in the cylinder space can be achieved thereby. In principle, this is however also possible by designing the helical gear particularly precisely, for example by low-tolerance production. According to another embodiment, the helical gear is a ball helical gear. Ball helical gears work very precisely due to their construction.

According to another embodiment, the combined linear and pivot bearing has a guide sleeve and a round rod that is guided in the guide sleeve on the middle axis of the main body, wherein the guide sleeve is securely connected to the main body, and the round rod is securely connected to the adjusting wheel, or vice versa. With this embodiment, the combined linear and pivot bearing is designed with a particularly simple structure as a radial slide bearing. The guides sleeve and the round rod guided therein on the middle axis of the main body enables a particularly favorable ratio of the guide length to the guide diameter for precise guidance.

According to another embodiment, the guide sleeve is designed integrally with the main body, and/or the round rod is designed integrally with the adjusting wheel, or vice versa. The integral design of the components of the linear and pivot bearing with the main body and adjusting wheel achieves particularly precise guidance of the adjusting wheel with respect to the main body.

According to another embodiment, at least one sliding ring that slides in the guide sleeve is arranged on the round rod. The sliding ring and guide sleeve can form a particularly low-friction material pairing. This enables a particularly smooth and precise adjustable rotation of the adjusting wheel. According to another embodiment, an at least partially peripheral annular groove and/or an at least partially peripheral projection is present on the round rod in which, or on which, the sliding ring is held on the round rod.

According to another embodiment, the spindle nut is designed integrally with the adjusting wheel or with the main body, and/or the threaded spindle is a component that is fastened to the main body or adjusting wheel by means of a fastening means (such as a fastening screw).

According to another embodiment, the round rod is simultaneously designed as a spindle nut in that it is provided with an inner thread for screwing in the threaded spindle. A design simplification is thereby achieved.

According to another embodiment, the rotational decoupling is a pivot bearing that has a first and a second pivot bearing element that are not axially displaceable relative to each other and are rotatable relative to each other, wherein the first pivot bearing element is fastened to the adjusting wheel and the second pivot bearing element is fastened to the plunger. The embodiment of the rotational decoupling as a pivot bearing enables solutions with a particularly simple design. According to another embodiment, the pivot bearing is a radial bearing that is concentric with the main body, preferably a radial roller bearing. The roller bearing is for example a grooved ball bearing. Simple standard roller bearings can be used. According to an alternative embodiment, the pivot bearing is a slide bearing.

According to another embodiment, the plunger consists of one or more of the following materials: Metal or plastic, preferably aluminum, or another rigid, dimensionally stable material.

According to another embodiment, the plunger has a hollow cylindrical annular space on the side facing the first end face that is concentric with the middle axis of the plunger, in which the rotational decoupling is at least partially arranged. This enables a space-saving accommodation of the rotational decoupling. When the rotational decoupling is designed as a radial bearing, in particular as a radial roller bearing, the annular space can advantageously serve to accommodate retaining rings to fix the inner ring and outer ring of the roller bearing. According to another embodiment, the retaining rings consist of one or more of the following materials: Metal or plastic, preferably stainless steel, or another rigid, dimensionally stable material.

According to another embodiment, the plunger has at least one peripheral first plunger sealing ring and at least one peripheral second plunger sealing ring on both the inner perimeter and the outer perimeter, by means of which the plunger is sealed against the inner wall and the outer wall of the cylinder space. According to a preferred embodiment, the plunger sealing rings are made of an elastic plastic. A particularly smooth and effective seal of the plunger in the cylinder space can be achieved thereby. According to another embodiment, the plunger sealing ring consists of one or more of the following materials: Elastic plastic, natural rubber, preferably NBR (nitrile rubber) or preferably FKM (fluoroelastomer rubber).

According to another embodiment, on the outer edge of a disk-shaped cover wall, the adjusting wheel has a peripheral casing that at least partially overlaps the outer perimeter of the main body. In this embodiment, the adjusting wheel is designed like a pot. The inner structure of the displacement device is protected by the casing.

According to another embodiment, at least one component, selected from the adjusting wheel, threaded spindle and main body, has a position display for displaying the position of the plunger in the cylinder space. According to another embodiment, the position display is a dial or a pointer. For example, the position display is arranged on a head of the threaded spindle that projects upwards out of a central hole in the adjusting wheel. The position of the plunger can be read at the edge of the hole on the position display that preferably is a dial. Alternatively, the position display is arranged on the outer perimeter of the main body. The position of the plunger can be read at the bottom edge of the casing on the position display that preferably is a dial.

According to another embodiment, the cylinder space is connected to a ventilation valve that has a closed position in which it separates the cylinder space from the surroundings, and an open position in which it connects the cylinder space to the surroundings, as well as an actuating apparatus in order to bring the ventilation valve from the closed position into the open position and from the open position into the closed position. The ventilation valve can be used to quickly decrease an overpressure. For example, it is used when, as a consequence of a clog, an overpressure builds up in the microcapillary tube that could suddenly relax from the clog being released, whereby bubbles would be blown into the cell medium such that the user cannot see the cells and hence cannot continue to work. This can lead to a sample loss. A destruction of expensive or rare cells can be avoided by fast ventilation.

According to a preferred embodiment, the actuating apparatus is designed such that the ventilation valve can be brought from the closed position into the open position by manual actuation, wherein a return spring is pretensioned such that the ventilation valve independently returns to the closed position after the actuating apparatus is relieved by the operator.

According to another embodiment, a device foot is arranged on a second end face of the main body that faces away from the first end face. According to a preferred embodiment, the device foot is designed such that it prevents the displacement device from being displaced from a position and/or protects the displacement device from vibration. According to a preferred embodiment, the device foot is a solid disk, and/or comprises or consists of at least one rubber element and/or a nonslip mat and/or at least one magnet.

Another aspect of the present invention is a method for cell manipulation using the injector according to the disclosed invention. The injector according to the invention is in particular suitable for methods such as in vitro fertilization (IVF), intra-cytoplasmic sperm injection (ICSI), the transfer of mitochondria and/or cell nucleus transfer. According to another embodiment, these methods comprise the following steps: (a) connecting a microcapillary tube to the injector according to the invention; (b) selecting a cell to be manipulated; (c) bringing the microcapillary tube connected to the injector according to the invention closer to the selected cell; (d) upon contacting the surface (cell wall and/or cell membrane depending on the cell type) of the cell with the microcapillary tube, applying an underpressure via the injector to hold the cell.

For the actual injection process, a capillary filled with injection material is brought closer to the cell surface (cell wall and/or cell membrane depending on the cell type) of a cell and is pushed through the cell surface so that the capillary penetrates the cytoplasm (penetrating contact). Depending on the use, the capillary is positioned more precisely, for example in the pronucleus located in the cytoplasm or the nucleus itself. Via the injector according to the invention, an overpressure is applied to inject the injection material, in particular a solution, a suspension (such as a cell suspension, nucleic acid suspension, etc.), a cell (in particular a sperm), cell material, in particular cytoplasm, cytoplasm components such as mitochondria and/or a pronucleus, into the cytoplasm (the term cytoplasm also comprises particular regions of the cytoplasm such as the direct environment of the nucleus).

For a removal process, the capillary is brought closer to the cell surface (cell wall and/or cell membrane depending on the cell type) of a cell and is pushed through the cell surface so that the capillary penetrates the cytoplasm (penetrating contact). Via the injector according to the invention, an underpressure is applied in order to remove a cell component via the injector, in particular the cell nucleus, the pronucleus, mitochondria and/or other cell components. These listed methods are normally used in a medical, biotech, biochemical, cell biology and/or forensic laboratory.

The invention is explained in greater detail below with reference to the appended drawings of an exemplary embodiment. In the drawings:

FIG. 1e shows a section along line e-e from FIG. 1a;

In the present application, the terms "vertical" and "horizontal," "top" and "bottom" and the terms derived therefrom such as "above" and "below," "top side" and "bottom side" refer to an alignment of the displacement device in which the middle axis of the main body and adjusting wheel are aligned vertically, and the adjusting wheel is arranged at least partially above the main body.

The injector 1 has a displacement device 2, an injection tube 3 and capillary holder 4 in which a microcapillary tube 5 is held.

Figure 1A:
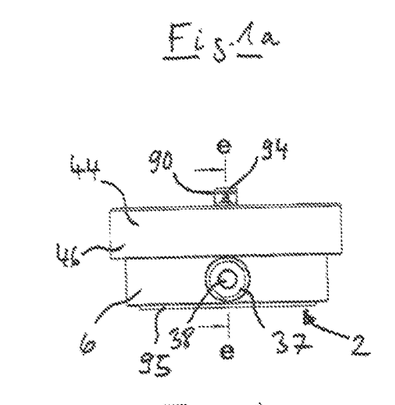
FIG. 1a shows a front view of a manual injector.
Figure 1B:
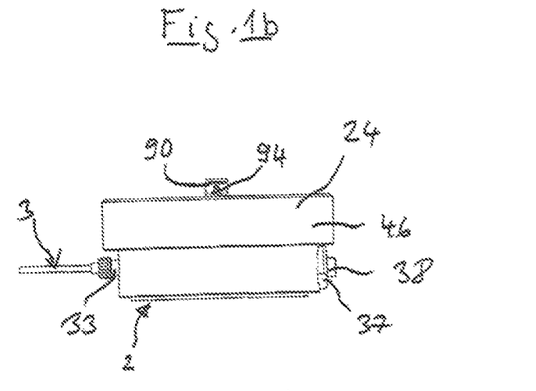
FIG. 1b shows a side view from the right side of the invention.
Figure 1C:
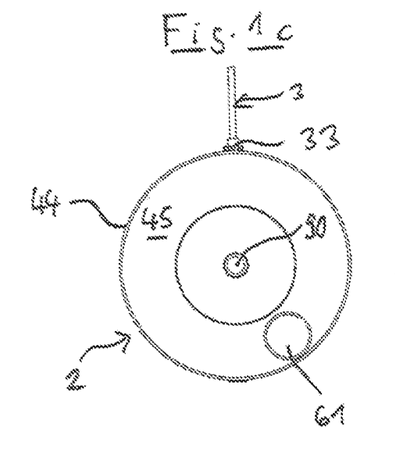
FIG. 1c shows a plan view of the invention.
Figure 1D:
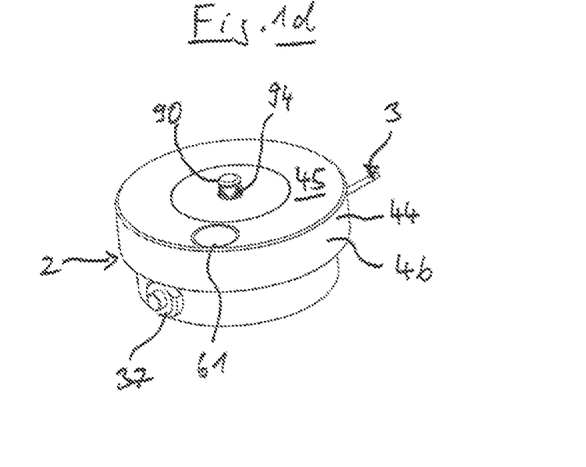
FIG. 1d shows a perspective view from above and from the side of the invention.
Figure 1E:
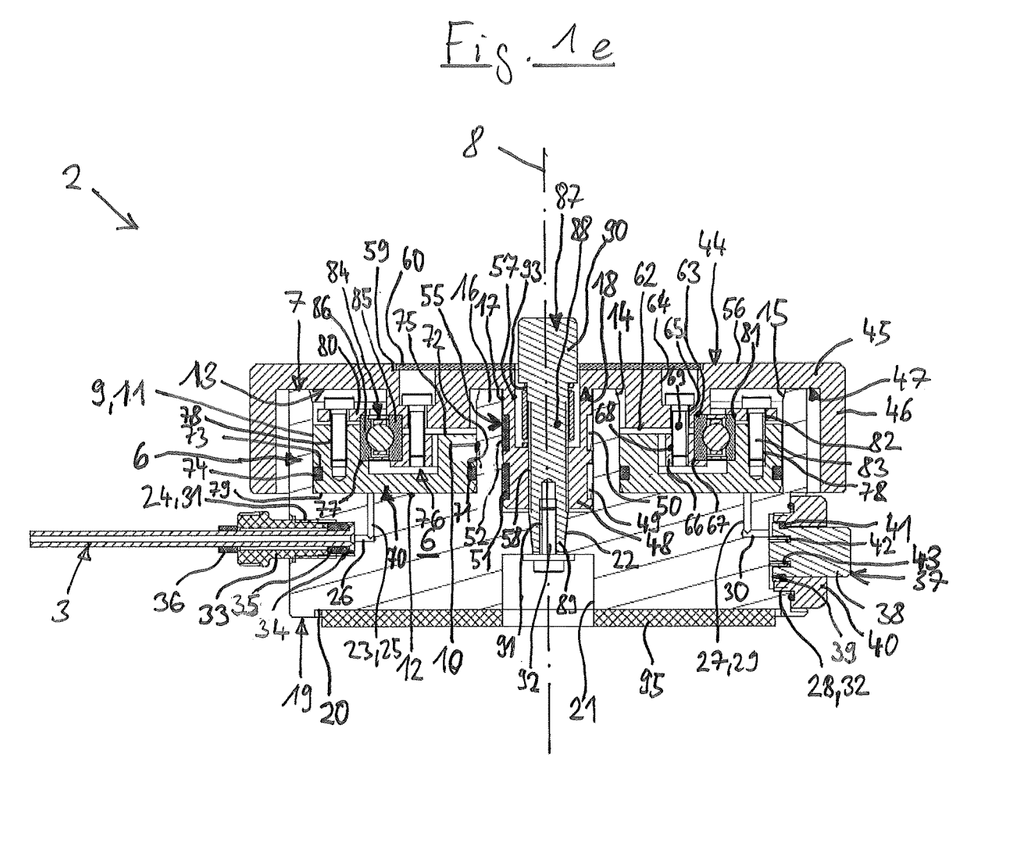
Figure 2:
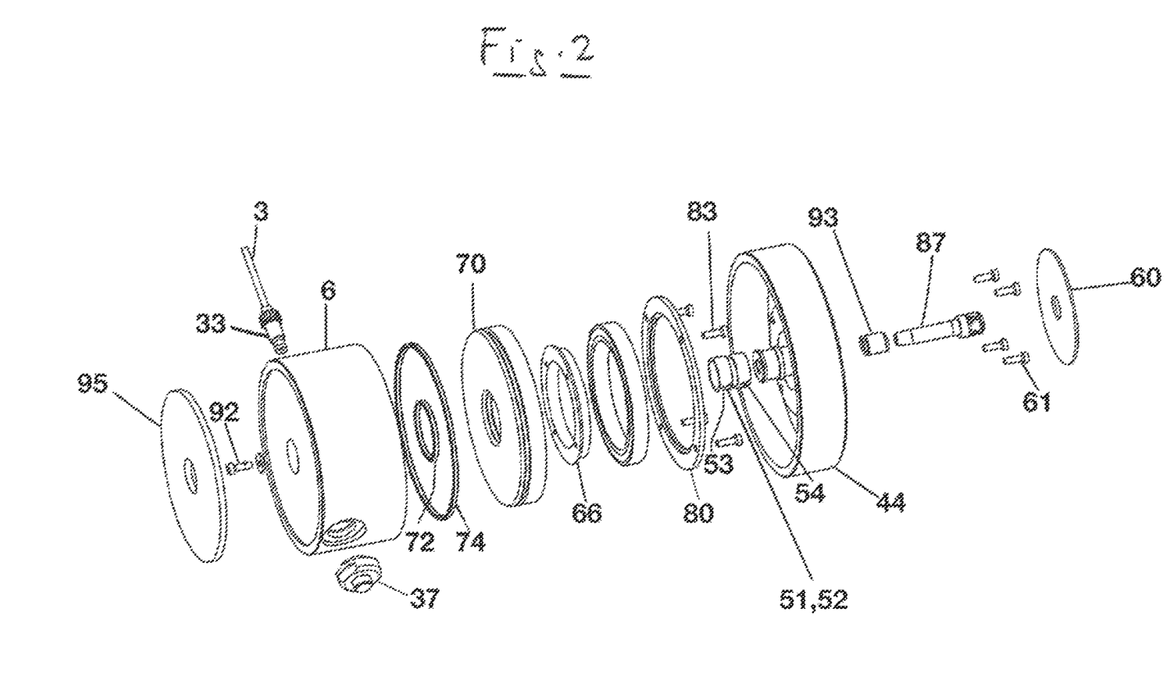
FIG. 2 shows the same injector in a perspective exploded view.

The displacement device 2 comprises a disk-shaped main body 6 that, on a first end face 7, has a hollow cylinder space 9 which is concentric with its middle axis 8. The cylinder space 9 has a cylindrical inner wall 10 and a cylindrical outer wall 11 as well as a disk-shaped floor wall 12.

The cylinder space 9 has an annular cylinder opening 13 in the first end face 7 through which it is accessible from the first end face 7. Both the inner wall as well as the outer wall 11 of the cylinder space 9 have a chamfer 14, 15 on the cylinder opening 13.

Furthermore, there is a guide sleeve 16 on the first end face 7 of the main body 6 with a middle axis that coincides with the middle axis 8 of the main body 6. The guide sleeve 16 is designed integrally with the main body 6, for example by introducing a central first blind hole 17.

The guide sleeve 16 has a sleeve opening 18 in the first end face 7 through which the guide sleeve 16 is accessible from a first end face 7.

The main body 6 has a disk-shaped first recess 20 in its second end face 19. Furthermore, the main body 6 has a central second blind hole 21 in the second end face 19 with a middle axis that coincides with the middle axis 8 of the main body 6. The second blind hold 21 has an opening in the second end face 19 through which it is accessible from the second end face 19.

Proceeding from the floor of the guide sleeve 16, a conical hole 22 that tapers from the guide sleeve 16 toward the second blind hole 21 extends to the floor of the second blind hole 21.

A first connecting channel 23 connects the cylinder space 9 to a third blind hole 24 that extends radially from the outer perimeter of the main body 6 thereinto. The first connecting channel 23 is formed by two intersecting channel holes 25, 26, of which one extends vertically into the main body from the floor wall 12 of the cylinder space 9, and the other extends from the floor of the third blind hole 24 radially into the main body 6.

Diametrically opposite the first connecting channel 23, the cylinder space 9 is connected via a second connecting channel 27 to a fourth blind hole 28 that extends from the perimeter of the main body 6 radially thereinto. The second connecting channel 27 is also formed by two intersecting channel holes 29, 30. The third and fourth blind hole 24, 28 are designed as threaded holes that each have an inner thread 31, 32.

A pressure-tight tube connection is designed as follows: a tube fitting 33 is screwed into the third blind hole 24 in order to connect the injection tube 3.

The tube fitting 33 is designed as a threaded sleeve. The tube fitting 33 seals the injection tube 3 against the base of the blind hole 24 by means of a tube flange 34 that is formed directly from the tube material of the injection tube 3. The tube fitting 33 is threaded onto the injection tube 3 in an axially movable manner and braces the tube flange 34 by means of the thread of the blind hold 24 against the base of the blind hole 24. A first sleeve 35 ensures the correct distance, and an O-ring on the perimeter of the first sleeve 35 is primarily used as a spring element, but also has an additional sealing effect.

A second sleeve 36 sits on the injection tube 3 and is braced against the outer end face of the tube fitting 33 and prevents it from slipping on the injection tube 3 before being screwed into the main body 6.

A ventilation valve 37 is arranged in the fourth blind hole 28. This has a valve knob 38 with a flange 39 on the inner end that is held in the fourth blind hole 28 by means of a union nut 40 screwed into the inner thread 32 of the fourth blind hole 28. In the shown home position, the flange 39 lies sealingly against to the inner end face of 41 of the union nut 40. The valve knob 38 has a peripheral central groove 42 in its inner end face in which a first helical spring 43 is inserted that is braced against the floor of the fourth blind hole 28. The valve knob 38 and helical spring 43 are an actuating apparatus.

Upon pressing in the valve knob 38, the helical spring 43 is compressed slightly, and a ventilation gap is opened between the valve knob 38 and union nut 40. Upon releasing the valve knob 38, the helical spring 43 presses the valve knob 38 back into the home position.

The main body 6 is for example produced as a single part from aluminum or another metal, or from plastic. It is preferably designed solid.

Furthermore, the displacement device 2 has an adjusting wheel 44 with a disk-shaped cover wall 45. A casing 46 runs around the outer edge of the cover wall such that the adjusting wheel 44 is pot-shaped overall.

A round rod 48 projects centrally from the second end face 47 of the cover wall 45 that faces the first end face 7 of the main body 6. The round bar 48 has two peripheral annular grooves 49, 50 on the outer perimeter. A sliding ring 51, 52 is inserted into each annular groove 49, 50. Each sliding ring 51, 52 has a slit 53, 54 that runs in the longitudinal direction and enables an expansion of the sliding ring 51, 52 in order to press it onto the round rod 48 and insert it into an annular groove 49, 50. The sliding rings 51, 52 project slightly beyond the outer perimeter of the round rod 48 and lie against the inner perimeter of the guide sleeve 16. Together with the guide sleeve 16, the round rod 48 forms a combined linear and pivot bearing 55 (linear pivot and slide bearing 55).

The adjusting wheel 44 has a central fifth blind hole 57 in its first end face 56. The round rod 48 is provided with a threaded hole 58 that extends in the round rod 48 from the floor of the central fifth blind hole 57 up to the second end face 47. The threaded hole 58 is designed as a spindle thread for receiving a threaded spindle.

The first end face 56 of the adjusting wheel 44 has a disk-shaped second recess 59. A cover disk 60 is arranged in the second recess 59. This consists for example of plastic, rubber or metal. It can in particular bear a dial or marking, or be made of a skin-friendly material.

In the first end face 56, the adjusting wheel 44 has a finger recess 61.

On its second end face 47, the cover wall 45 of the adjusting wheel 44 has a disk-shaped base 62 that is concentric with the round rod 48. The base 62 has a peripheral first shoulder 63 between the outer perimeter and bottom side. Sixth blind holes 64 extend into the adjusting wheel 44 from the first end face 56 of the cover wall 45 parallel to the round rod 48. Proceeding from the floor of the sixth blind holes 64, through-holes 65 extend up to the bottom side of the base 62.

The adjusting wheel 44 is for example produced from aluminum or another metal, or from plastic. The adjusting wheel 44 is preferably produced as a single part.

A bottom retaining ring 66 is arranged below the base 62 and has a second shoulder 67 on the outer perimeter. The bottom retaining ring 66 has first threaded holes 68. It is held on the adjusting wheel 44 by means of first fastening screws 69 that are inserted into the sixth blind holes 64, penetrate the through-holes 65 and are screwed into the first threaded holes 68, and their screw heads are braced against the floor of the sixth blind holes 64.

A plunger 70 is arranged in the cylinder space 9 and substantially has the shape of a circular disk. On the inner perimeter, the plunger 70 has a peripheral first plunger annular groove 71 in which a first elastic plunger sealing ring 72 is seated. On the outer perimeter, it has a second peripheral plunger annular groove 73 in which an elastic second plunger sealing ring 74 is seated. The first plunger sealing ring 72 seals the plunger 70 against the inner wall of the cylinder space 9, and the second plunger sealing ring 74 seals the plunger 70 against the outer wall of the cylinder space 9.

On its first end face 75 that faces the cylinder opening 13 of the cylinder space 9, the plunger 70 has a hollow cylindrical annular space 76 that is concentric with the middle axis of the plunger 70. The annular space 76 has a third shoulder 77 in the outer wall. Furthermore, it has second threaded holes 78 in its first end face 75 that extend parallel to its middle axis. The second end face 79 of the plunger 70 is smooth and forms the plunger floor.

The plunger 70 is for example produced from plastic or metal.

A disk-shaped top retaining ring 80 is arranged above the plunger 70 and has a fourth shoulder 81 on the inner perimeter. The top retaining ring 80 has through-holes 82 that extend parallel to the middle axis of the plunger 70. Second fastening screws 83 extend through the through-holes 82 and are screwed into the second threaded holes 78 of the plunger 70 until the heads of the second fastening screws 83 lie on the top side of the top retaining ring 80.

Furthermore, the displacement device 2 comprises a roller bearing 84 that is designed as a grooved ball bearing. The roller bearing 84 is arranged between the adjusting wheel 44 and plunger 70. At the top, the inner ring 85 of the roller bearing 84 is braced against the first shoulder 63 on the base 62 of the adjusting wheel 44 and, at the bottom, is braced against the second shoulder 67 of the bottom retaining ring 66.

The inner ring 85 is clamped tightly by tightening the bottom retaining ring 66 by means of the first fastening screws 69.

The outer ring 86 of the roller bearing 84 is braced between the third shoulder 77 of the plunger 70 and the fourth shoulder 81 of the top retaining ring 80, and is clamped tightly between the top retaining ring 80 and plunger 70 by tightening the second fastening screws 83.

The roller bearing 84 securely holds the plunger 70 in a defined axial position relative to the adjusting wheel 44 and enables the adjusting wheel 44 to rotate relative to the plunger 70. This forms a rotational decoupling between the adjusting wheel 44 and plunger 70.

Furthermore, the displacement device 2 comprises a threaded spindle 87. This has a spindle shaft 88 with a cone 89 at the bottom end, and a spindle head 90 at the top end. A third threaded hole 91 is arranged in the bottom end face of the threaded spindle 87 on the middle axis of the threaded spindle 87.

The threaded spindle 87 is for example produced from plastic or metal.

The threaded spindle 87 is inserted into the fifth blind hole 57 of the adjusting wheel 44 and is screwed into the threaded hole 58 in the round rod 48. The cone 89 is inserted into the conical hole 22 in the main body 6. The threaded spindle 87 is fixed in the main body 6 by means of a third fastening screw 92 introduced from below into the second blind hole 21 in the main body 6. A second helical spring 93 is guided on the perimeter of the threaded spindle 87 between the spindle head 90 and the floor of the fifth blind hole 57 of the adjusting wheel 44. The second helical spring 93 serves to take up the play between the threaded spindle 87 and threaded hole 58.

The spindle head 90 has a position display 94 with a dial on the outer side.

A disk-shaped device foot 95 is arranged in the first recess 20 and for example is designed as a rubber disk, magnetic disk or sticky pad.

Figure 3:
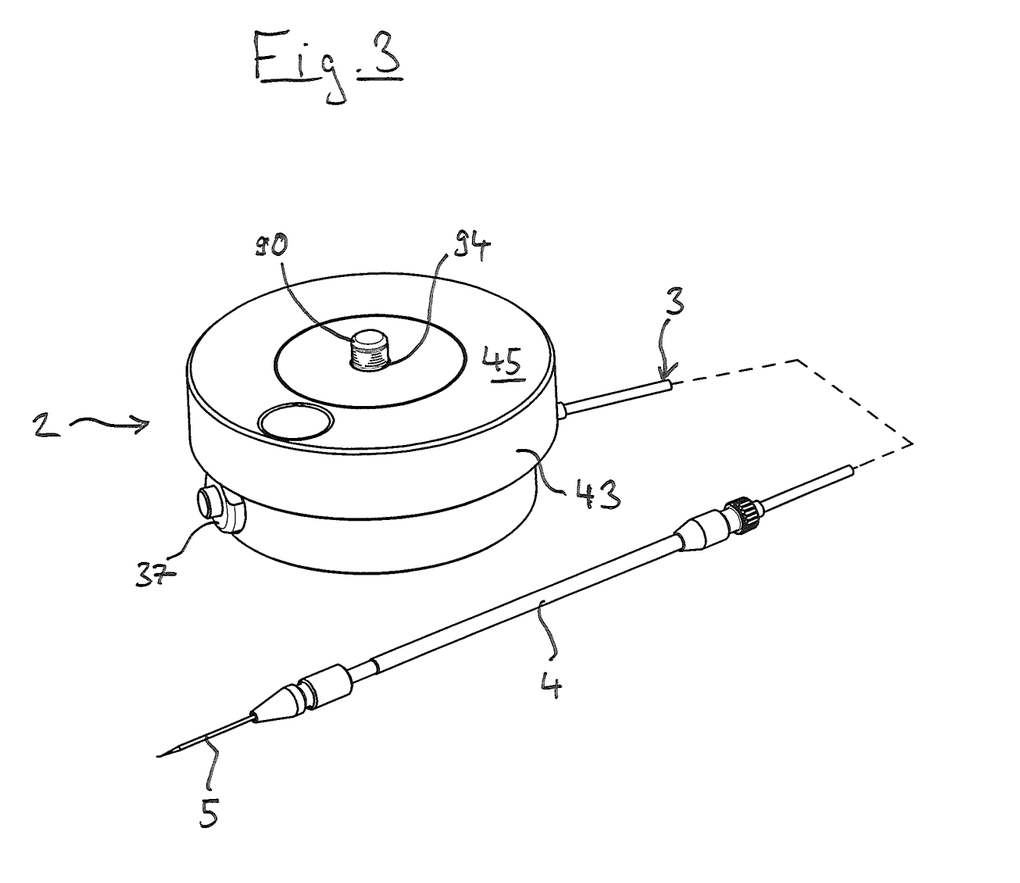
FIG. 3 shows the same injector with an injection tube together with a capillary holder and a microcapillary tube.

The other end of the injection tube 3 is connected to the capillary holder 4. The capillary holder 4 is tubular and designed to clamp the exchangeable microcapillary tube 5.

While the adjusting wheel 44 is rotating, its threaded hole 58 executes a screwing movement on the threaded spindle 87. In so doing, the adjusting wheel 44 is guided by the bearing of the round rod 48 in the guide sleeve 16 in the longitudinal direction and radial direction precisely relative to the main body 6. Since the threaded spindle 87 is fixed in the main body 6, the adjusting wheel 44 is displaced axially relative to the main body 6. Depending on the direction of rotation of the adjusting wheel 44, it moves axially downward or upward. Due to the connection of the adjusting wheel 44 via the roller bearing 84 to the plunger 70, the plunger 70 is also displaced in the axial direction but does not also rotate, and a rotational decoupling therefore exists between the adjusting wheel 44 and plunger 70.

Due to the displacement of the plunger 70, air is displaced in the cylinder space 9, and an air column is shifted in the injection tube 3. Due to the shifting of the air column, material can be ejected from the microcapillary tubes 5 or drawn into or held therein.

REFERENCE NUMBER LIST

1 Injector
2 Displacement device

3 Injection tube
4 Capillary holder
5 Microcapillary tube
6 Main body
7 First end face
8 Middle axis
9 cylinder space
10 Inner wall
11 Outer wall
12 Floor wall
13 Cylinder opening
14, 15 Chamfer
16 Guide sleeve
17 First blind hole
18 Sleeve opening
19 Second end face
First recess
21 Second blind hole
22 Conical hole
23 First connecting channel
24 Third blind hole
25, 26 Channel holes
27 Second connecting channel
28 Fourth blind hole
29, 30 Channel holes
31, 32 Inner thread
33 Tube fitting
34 Tube flange
35 First sleeve
36 Second sleeve
37 Ventilation valve
38 Valve knob
39 Flange
40 Union nut
41 End face
42 Groove
43 Helical spring
44 Adjusting wheel
45 Cover wall
46 Casing
47 End face
48 Round rod
49, 50 Annular grooves
51, 52 Sliding ring
53, 54 Slit
55 Combined linear and pivot bearing
56 End face
57 Fifth blind hole
58 Threaded hole
59 Recess
60 Cover disk
61 Finger recess
62 Base
63 First shoulder
64 Sixth blind hole
65 Through-holes
66 Bottom retaining ring
67 Second shoulder
68 Threaded holes
69 First fastening screws
70 Plunger
71 First peripheral plunger annular groove
72 First plunger sealing ring
73 Second peripheral plunger annular groove
74 Second plunger sealing ring
75 End face
76 Annular space
77 Third shoulder
78 Second threaded holes
79 Second end face
80 Top retaining ring
81 Fourth shoulder
82 Through-holes
83 Second fastening screws
84 Roller bearing
85 Inner ring
86 Outer ring
87 Threaded spindle
88 Spindle shaft
89 Cone
90 Spindle head
91 Third threaded hole
92 Third fastening screw
93 Second helical spring
94 Position display
95 Device foot

The invention claimed is:

1. A manual injector for cell manipulation comprising a displacement device (2) for displacing a fluid, an injection tube (3) connected to the displacement device (2), and a capillary holder (4) connected to the injection tube (3) for holding a microcapillary tube (5) or a microcapillary tube (5) connected to the injection tube (3), wherein the displacement device (2) has the following features:
a disk-shaped main body (6) that, on a first end face (7), has a hollow cylinder space (9) which is concentric with its middle axis (8),
a disk-shaped adjusting wheel (44) which is concentric with the main body (6) and is arranged on the first end face (7),
a helical gear comprising a spindle nut and a threaded spindle (87) engaging therein and arranged on the middle axis (8) of the main body (6), wherein the spindle nut is securely connected to the adjusting wheel (44), and the threaded spindle (87) is securely connected to the main body (6) or vice versa,
a hollow cylindrical plunger (70) arranged in the cylinder space (9) and sealingly adjacent to an inner perimeter of an inner wall (10) of the cylinder space (9) and an outer perimeter of an outer wall (11) of the cylinder space (9),
a rotational decoupling that connects the adjusting wheel (44) to the plunger (70) and is designed such that the plunger (70) and adjusting wheel (44) are not displaceable relative to each other in the direction of the middle axis (8) of the main body (6), and are rotatable relative to each other about the middle axis (8), and
a connection (33) connected to the cylinder space (9) to which the injection tube (3) is connected.

2. The injector according to claim 1, in which a combined linear and pivot bearing (55) is present between the main body (6) and adjusting wheel (44) and is designed to guide the adjusting wheel (44) axially in the direction of the middle axis (8) of the main body (6) when displaced relative to the main body (6), and to radially bear the adjusting wheel (44) about the middle axis (8) of the main body (6).

3. The injector according to claim 2, in which the combined linear and pivot bearing (55) has a hollow cylindrical guide sleeve (16) and a round rod (48) that is guided in the guide sleeve (16) on the middle axis (8) of the main body (6), wherein the guide sleeve (16) is securely connected to the main body (6) and the round rod (48) is securely connected to the adjusting wheel (44), or vice versa.

4. The injector according to claim 3, in which the guide sleeve (16) is designed integrally with the main body (6) and/or the round rod (48) is designed integrally with the adjusting wheel (44), or vice versa.

5. The injector according to claim 3, in which at least one sliding ring (51, 52) that slides in the guide sleeve (16) is arranged on the round rod (48).

6. The injector according to claim 1, in which the spindle nut is designed integrally with the adjusting wheel (44) or main body (6) and/or the threaded spindle (87) is a component that is fastened to the main body (6) or adjusting wheel (44) by means of a fastening means (92).

7. The injector according to claim 3, in which the round rod (48) is simultaneously designed as a spindle nut in that it is provided with an inner thread (31, 32) for screwing in the threaded spindle (87).

8. The injector according to claim 1, in which the rotational decoupling is a pivot bearing (84) that has a first and a second pivot bearing element (85, 86) that are not axially displaceable relative to each other and are rotatable relative to each other, wherein the first pivot bearing element (85) is fastened to the adjusting wheel (44), and the second pivot bearing element (86) is fastened to the plunger (70).

9. The injector according to claim 8, in which the pivot bearing is a radial bearing that is concentric with the main body (6), preferably a radial roller bearing (84).

10. The injector according to claim 1, in which the plunger (70) has a hollow cylindrical annular space (76) on the side facing the first end face (7) that is concentric with the middle axis (8) of the plunger (70), and in which the rotational decoupling is at least partially arranged.

11. The injector according to claim 1, in which the plunger (70) bears at least one first plunger sealing ring (72) on the inner perimeter and at least one second plunger sealing ring (74) on the outer perimeter by means of which the plunger (70) is sealed against the inner wall of the cylinder space (9) and the outer wall (11) of the cylinder space (9).

12. The injector according to claim 1, in which, on an outer edge of a disk-shaped cover wall (45), the adjusting wheel (44) has a peripheral casing (46) that at least partially overlaps the outer perimeter of the main body (6).

13. The injector according to claim 1, wherein the adjusting wheel (44), the threaded spindle (87) or the main body (6), has a position display (94) for displaying the position of the plunger (70) in the cylinder space (9).

14. The injector according to claim 1, in which the cylinder space (9) is connected to a ventilation valve (37) that has a closed position in which it separates the cylinder space (9) from the surroundings, and an open position in which it connects the cylinder space (9) to the surroundings, as well as an actuating apparatus in order to bring the ventilation valve (37) from the closed position into the open position, and from the open position into the closed position.

15. The injector according to claim 1, wherein, on a second end face (19) of the main body (6) that faces away from the first end face (7), a device foot (95) is arranged that comprises or consists of a solid disk and/or at least one rubber element and/or at least one magnet.

16. A method for cell manipulation comprising the following steps:
(a) selecting a cell to be manipulated;
(b) bringing a microcapillary tube connected to the injector according to claim 1 closer to the selected cell;
(c) when the microcapillary tube contacts the cell, applying an underpressure via the injector to hold the cell; or
(d) when the microcapillary tube contacts and penetrates the cell, generating an overpressure via the injector to inject a solution, a cell, in particular a sperm, and/or cell components; or
(e) when the microcapillary tube contacts and penetrates the cell, generating an underpressure via the injector to remove a cell component, in particular a cell nucleus or a pronucleus.

17. The method for cell manipulation according to claim 16 for in vitro fertilization (IVF), intra-cytoplasmic sperm injection (ICSI), transferring mitochondria and/or cell nuclei.

\* \* \* \* \*